United States Patent [19]
Werstiuk et al.

[11] 3,989,705
[45] Nov. 2, 1976

[54] PROCESSES FOR THE DEUTERATION AND/OR TRITIATION OF ORGANIC SUBSTRATES BY HYDROGEN SUBSTITUTION

[75] Inventors: Nick Henry Werstiuk, Hamilton; Tonu Kadai, Beaconsfield, both of Canada

[73] Assignee: Canadian Patents and Development Limited, Ottawa, Canada

[22] Filed: Apr. 1, 1974

[21] Appl. No.: 456,935

[52] U.S. Cl. .......................... 260/290 P; 260/250 R; 260/251 R; 260/252; 260/283 R; 260/302 R; 260/307 R; 260/309; 260/310 R; 260/329 R; 260/346.1 R; 260/613 D; 260/621 R; 260/622 R; 260/623 R; 260/624 R; 260/668 R
[51] Int. Cl.$^2$ ...................................... C07D 213/04
[58] Field of Search ......... 260/290 P, 621 R, 624 R, 260/623 R

[56] References Cited
OTHER PUBLICATIONS

Chemical Abstracts I, vol. 46, Col. 10114 (abst. of Bell) (1952).
Chemical Abstracts II, vol. 52, Cols. 14683–14684 (abst. of Israeli Pat. 10,518) (1958).
Chemical Abstracts III, vol. 54, Cols. 18395–183956 (abst. of Alipranidi et al.) (1960).
Chemical Abstracts IV, vol. 54 Col. 23643 (abst. of Rekasheva et al.) (1960).
Chemical Abstracts V, abst. of Zilberman Cols. 658–657 (1962) (vol. 57).
Chemical Abstracts VI, Abst. of Gordon et al., Cols. 5337–5338 (1962).
Chemical Abstracts VII, vol. 57, Cols. 7733 and 7734 (abstracts of Kursanov et al. and Fenimore et al.) (1959).
Chemical Abstracts VIII, vol. 59, Cols. 8693–8694 (Mantescu et al.) 1963.
Chemical Abstracts IX, vol. 66, abst. No. 55735h (1967).
Brullmann et al., Helv. Chim. Acta vol. 41, pp. 1831 to 1835 (1958).
Werstiuk et al., (I) Chemical Communications 1971, pp. 1349 to 1350.
Werstiuk et al. (II), Canadian Journal of Chemistry, vol. 51, pp. 1485 to 1486 (May 1973).

*Primary Examiner*—John D. Randolph
*Attorney, Agent, or Firm*—Hirons & Rogers

[57] ABSTRACT

In processes for the deuteration and/or tritiation of cyclic organic substrates by hydrogen substitution, the substrate is subjected at a temperature of between about 200° and 400° C to the effect of a 0.10% to 10% V/V dilute solution of a strong acid in the respective oxide constituting the isotope pool for the exchange. A deuterated or tritated acid may be used. Rapid exchange in the aromatic ring and high yields are obtained with apparent freedom from side reactions and decomposition.

10 Claims, No Drawings

PROCESSES FOR THE DEUTERATION AND/OR TRITIATION OF ORGANIC SUBSTRATES BY HYDROGEN SUBSTITUTION

FIELD OF THE INVENTION

The present invention is concerned with processes for the deuteration and/or tritiation of organic substrates by hydrogen substitution and the products of such processes.

REVIEW OF THE PRIOR ART

The "labelling" of organic compounds by substitution of hydrogen atoms thereof with deuterium or tritium is now a well-established procedure in view of the many uses to which such labelled compounds can be put, and efforts are now directed to the provision of processes for deuteration and/or tritation that are economical and result in the highest possible yields of specific compounds.

For convenience in the language used in the descriptive part of the specification and in the claims, but not in the specific examples, when reference is made to deuterium and deuteration it is intended to include also tritium and tritiation, or a mixture of deuterium and tritium. Some common methods used hitherto for the introduction of one or more deuterium atoms into organic molecules are, for example, (a) acid-and base-catalyzed exchange of carbonyl containing compounds, (b) metal deuteride reductions, (c) reduction by use of metallic sodium or potassium in deuterated alcohol, (d) catalytic deuteration of double bonds, (e) chromatographic exchange, (f) metal-catalyzed (homogeneous and heterogeneous) exchange, (g) base-catalyzed exchange via carbanions and (l) acid-catalyzed exchange via carbonium ions. Of these, only the last three have been used extensively for perdeuteration.

Metal-catalyzed (homogeneous and Heterogeneous) exchange has been the most popular method hitherto but suffers from the following deficiencies:

i. irreproducibility of catalytic surfaces and results
ii. the catalyst surface has many different types of sites available to the molecule and each of these may have its own characteristics in isotopic exchange reactions
iii. incidental poisoning of the catalyst by the organic molecule being exchanged or poisoning by an accidentally or deliberately introduced extraneous species
iv. complicated and expensive apparatus
v. steric hinderance in certain molecules
vi. side reactions such as coupling of aromatic rings
vii. low deuterium incorporation, thus making it necessary for multi-stage equilibrations using fresh catalyst and deuterium oxide.

The main disadvantages of base-catalyzed exchange via carban ions are:

i. sometimes undesired side reactions occur faster than the desired exchange and reagents must be chosen carefully to block out undesired side reactions
ii. often very strongly basic and/or high temperatures (400° C) conditions must be used in order to get an effective exchange process to occur. This can become very expensive and inconvenient.

Acid-catalyzed exchange methods which increase the extent and the rate of deuterium incorporation are mostly concerned with raising the acidity of the deuterium source while trying to maintain a minimum amount of decomposition that this increase of acidity may cause. Some of the various mixtures used are for example liquid deuterium bromide, acetic acid with stannic chloride, deuterated phosphoric acid, deuterium chloride, deuterated phosphoric acid-boron trifluoride complex in liquid sulfur dioxide, 50–80% deuterium sulphate in water, fluorosulfonic acid-antimony pentafluoride complex ("magic acid"). Many of these systems, however, are unsatisfactory because of cost, complicated apparatus and procedures, slow or incomplete exchange, and low yields (due to sulfonation, decomposition, etc).

It is the principal object of the present invention to provide new processes for the deuteration and/or tritation of organic substrates.

DEFINITION OF THE INVENTION

In accordance with the present invention there is provided a process for the deuteration or tritiation of organic substrates e.g. of the kind specified hereinafter, by hydrogen substitution, the substrate containing unsaturation and being capable of carbonium ion formation at the site of the unsaturation wherein the substrate is subjected to the effects of a 0.10 to 10% V/V dilute solution of a strong acid in deuterium oxide or tritium oxide respectively at a temperature between about 200° and 400° C.

It will be seen that, in general, a process in accordance with the invention uses relatively high temperature and relatively dilute acid. Carbonium ions are high-energy ion-deficient species which therefore have cationic properties and can be neutralized by attack of a neucleophile or loss of a proton. It is believed that this property of carbonium ions is the basis of the exchange that takes place in the processes of the invention.

Such processes are believed to present substantial advantages, as compared to the labelling procedures discussed above, as follows:

a. The processes use the cheapest deuterium source presently available,
b. the use of dilute acid reduces the quantity required (and thereby the cost directly), besides simplifying and reducing the cost of the subsequent elimination of unused acid,
c. excellent yields are obtained at high speeds, so that in many cases a one-step process is sufficient, while almost all cases not satisfactory with one step are satisfactory with two steps,
d. apparent freedom from steric effects,
e. apparent freedom from side reactions,
f. relative freedom from decomposition except, of course, in the case of substrates in which decomposition will inherently be obtained at the temperature of operation,
g. it is possible to obtain substitution in the ring system of various side-chain substituted aromatic compounds without appreciable substitution in the side chains, and such capability has not been demonstrated in any of the prior processes known to us,
h. in the substitutions specified in the preceding paragraph it is possible to obtain selective substitution in the different ring positions.

In general, processes in accordance with the invention can be expressed by the relation

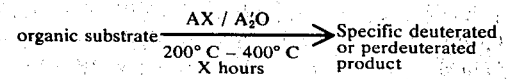

where AX is a strong acid with A = Hydrogen, deuterium or tritium or any mixture thereof, and A' is deuterium and/or tritium.

The strong acid may be, for example, any one of ACl ABr; $A_2SO_4$; $A_3PO_4$; $ANO_3$; and $CF_3COOA$, and preferably is ACl. Acetic acid $CH_3COOA$ may also be used successfully although it is usually classified as a weak acid, since in the temperature range specified for the processes of the invention it is operative as a strong acid; typically it is used in processes in which the substrate is itself highly reactive.

Preferably the substrate is subjected to the effect of a 0.10 to 4% V/V dilute solution of the concentrated acid; very effective yields are obtained at these high dilutions, as will be illustrated by the examples given below, with increasing benefit in economy and ease of operation of the process. In some processes a more restricted range of 0.25-2% V/V is adequate.

The preferred temperature range is 200° to 350° C, since in this range the benefit of the higher temperatures are obtained, but difficulties that may be experienced because of degradation of the product due to temperature effects are not so apparent. Owing to the temperatures at which the processes are carried out the reactions must take place in sealed vessels, so that the constituents are subjected to pressures corresponding to the vapour pressure of the system at the particular temperature. For the temperature range 200° to 400° C therefore these pressures will be in the range about 100 to 5,000 p.s.i., more specifically about 100 to 3,000 p.s.i.

As indicated by the general expression above a hydrogen-based acid can be used, in view of its very high dilution by the deuterium oxide, although for maximum yield the available isotope pool should be made as large as possible, and it is therefore preferred to use the corresponding deuterated or tritated acid.

The organic substrates employed in the processes of the invention are selected from the group consisting of aromatic compounds, substituted aromatic compounds, polynuclear aromatic compounds, and heterocyclic compounds. All of the compounds to which the process is applicable are characterized by the capability of carbonium ion formation, e.g. by the presence of a double bond.

More specific examples of suitable organic substrates are:

i. Aromatic compounds such as benzene, mono-and poly-substituted alkyl benzenes, aminobenzenes, hydroxybenzenes, alkoxybenzenes, phenol carboxylic acids, nitro-compounds benzenes, halobenzenes, phenyl alkyl carboxylic acids (with such substitution on the phenyl grouping and/or the side chain), specifically aniline, phenol, benzoic acid, toluene, o-and p-xylene, t-butylbenzene, bromo-benzene, chlorobenzene, methoxybenzene and anisole.

ii. Mono-and poly-substituted polybenzenes, specifically bi-phenyl.

iii. Polynuclear compounds of substituted and non-substituted types, such as napthalenes, anthracenes, phenanthrenes, specifically napthalene, anthracene, acenapthlene, chrysene, coronene and phenanthrene.

iv. Heterocyclics having aromatic characteristics such as six-membered rings containing one nitrogen, exemplified by pyridines; six membered rings containing more than one nitrogen exemplified by pyrazines, pyridazines, and pyrimidines; polynuclear heterocyclics exemplified by quinolines, isoquinolines and purines; five membered rings containing only one heteroatom (O, N or S) exemplified by the furans, pyrroles and thiophenes, and five membered rings containing several heteroatoms exemplified by the imidazoles, pyrazoles, thiazoles and oxazoles, specifically furan, thiophene and pyridine.

Specific embodiments of the invention will now be described, by way of example.

EXAMPLE 1

0.622g of benzene and 15 ml of 4% V/V conc. HCl in $D_2O$ were introduced into a glass tube measuring 11 inches × 0.5 inch. The sample was degassed three times by the freeze-pump-thaw method, sealed and heated at 250° C for 48 hours in a Model 4914 Pressure Reaction Apparatus sold by Parr Instrument Company. The resultant colourless two-phase reaction mixture was separated by a separator funnel to yield 0.608g benzene of greater than 95% purity for a 98% yield. Deuterium assay by mass spectrometry at 15 eV showed that an 88% exchange of hydrogen atoms for deuterium atoms had taken place, so that 5.26 deuterium atoms had been incorporated into the benzene. Deuterochloric acid can be used in place of hydrochloric acid to increase the isotope pool.

EXAMPLES 2 through 6

The following examples listed in Table 1 show the degree of exchange to be obtained in benzene substrate with different acid concentrations in the process. These examples show that only a 1.5-2% V/V concentration of acid is required at 250° C for complete exchange (to equilibration) of the benzene in 24 hours. There is no advantage in such process in using acid concentrations much above 1.5-4% or 2-4%, and with these low dilutions side reaction and decompositions were minimal. The exchange time can be reduced by carrying out the processes at higher temperatures e.g. 275° to 300° C.

In each example 0.7g of benzene, the appropriate volume of conc. DCl in $D_2O$, and sufficient $D_2O$ to make the $D_2O$ solution up to 10 ml (approximately 0.5 mole) were sealed under vacuum in a glass tube after two freeze-pump-thaw cycles. The tubes were heated at 250° for 24 hours, cooled, opened and the contents were analyzed for deuterium content by n.m.r. integral analysis. Anhydrous methanol was weighed out as the internal standard for the integral analysis.

TABLE 1

| Example | Temperature° C | Time | Acid Conc V/V | % Exchange |
| --- | --- | --- | --- | --- |
| 2 | 250° C | 24 Hrs. | 0.25 | 37 |
| 3 | 250° C | 24 Hrs. | 0.50 | 75 |
| 4 | 250° C | 24 Hrs. | 2.00 | 98 |
| 5 | 250° C | 24 Hrs. | 7.00 | 99 |
| 6 | 250° C | 24 Hrs. | 10.00 | 99 |

EXAMPLES 7 and 8

Table 2 below gives corresponding results obtained using phenol as the substrate and a 4% V/V solution of concentrated hydrochloric acid in deuterium oxide. The number of deuterium atoms per molecule was determined by mass spectroscopy after residual acid was washed out, and also by n.m.r. integral analysis. The percent recovery at 175° C was not determined.

TABLE 2

| EX. | Conditions Temp.° C | Time (h) | D/molecule | % Exchange in aromatic ring | Position O | + p | % Recovery |
|---|---|---|---|---|---|---|---|
| 7 | 175 | 72 | 3.05 | 61 | 2.7 | 0.2 | — |
| 8 | 200 | 48 | 3.90 | 78 | 2.7 | 1.3 | 95 |

EXAMPLES 9 and 10

Table 3 below shows some further results using phenol as the substrate. In example 9 the acid used was 10% V/V of CH$_3$COOD in D$_2$O, while that in example 10 consisted of that of example 9 with the addition of 1% V/V conc HCl. The increase of deuteriation in example 10 will be observed.

TABLE 3

| Example | Temp. ° C | Time | D/Mol | Position of D | Yield |
|---|---|---|---|---|---|
| 9 | 260 | 53 | 2.57 | ring | 72 |
| 10 | 260 | 53 | 3.91 | ring | 53 |

EXAMPLES 11 to 13

Table 4 below gives corresponding results for benzoic acid as the substrate, using the same 4% V/V solution as for phenol. The failure of Example 11 to achieve substitution will be noted. The number of deuterium atoms per molecule was determined by n.m.r. integral analysis using the back-exchanged O—H as an internal standard. It will be seen that a single step process is completely adequate for almost maximum exchange (94%) to take place.

TABLE 4

| Example | Temp.° C | Time | D/mol. | % Exchange in ring | % Recovery |
|---|---|---|---|---|---|
| 11 | 175 | 72 | 0 | 0 | 95% |
| 12 | 250 | 65 | 3.40 | 68 | 95% |
| 13 | 275 | 75 | 4.70 | 94 | 97% |

EXAMPLES 14 to 18

In each example 0.87g of toluene, the appropriate volume of conc. DCl in D$_2$O and sufficient D$_2$O to make the D$_2$O solution up to 10 ml (approximately 0.5 mole) were sealed under vacuum in a glass tube after two freeze-pump-thaw cycles. The tubes were heated in a 2 l Parr bomb (with water and toluene added to equalize pressure) at 250° for 24 hours. N.m.r. integral analysis using the methyl group (which does not undergo exchange) as internal standard established the degree of exchange on the aromatic ring as a function of acid concentration. The resultant data is shown in Table 5. The results establish that only 0.5–1% V/V conc. DCl in D$_2$O is required to completely exchange (to equilibration) the aromatic protons in toluene (toluene to D$_2$O molar ratio of 1:50) after 24 hours at 250°. The exchange time at these acid concentrations can be reduced by carrying out the reaction at 275°–300°. As with the comparable results for benzene given in Table 1, when plotted these results show that a satisfactory degree of deuteration (tritiation) will be achieved with acid concentrations as low as 0.10% V/V in D$_2$O, and an especially suitable range will be 0.1–3%.

TABLE 5

| Example | Temp.° C | Time (h) | Acid Conc V/V | % Exchange |
|---|---|---|---|---|
| 14 | 250 | 24 | 0.25 | 51 |
| 15 | 250 | 24 | 0.50 | 95 |
| 16 | 250 | 24 | 2.00 | 99.5 |
| 17 | 250 | 24 | 7.00 | 99.5 |
| 18 | 250 | 24 | 10.00 | 99.0 |

EXAMPLE 19

0.387g of biphenyl and 15 ml of 4% V/V conc. HCl in D$_2$O were introduced into a glass tube. The sample was degassed three times by the freeze-pump-thaw method, sealed and heated at 250° in the Pressure Reaction Apparatus for 48 hours. The colourless oil solidified on cooling. The reaction mixture was neutralized with solid NaHCO$_3$ and extracted with ether (4 × 15 ml). The combined either extracts were dried over anhydrous magnesium sulphate, filtered and concentrated on a rotary evaporator. Final traces of ether were removed by use of vacuum to yield 0.380g solid biphenyl of 98% purity. Deuterium assay by mass spectrometer at 15 eV established that 9.39 deuterium atoms had been incorporated into the biphenyl, constituting a 94% exchange.

EXAMPLE 20

50g of o-xylene and 200 ml of 4% V/V DCl in D$_2$O were added to the Pressure Reaction Apparatus fitted with a glass liner. After heating for 43 hours, the resulting two phase reaction mixture was separated by separator funnel to give a 90% yield of yellowish 45g xylene of greater than 95% purity. Using anhydrous methanol as an internal standard, nuclear magnetic resonance integral analysis established that 3.50 deuterium atoms had been incorporated into the aromatic ring (88% exchange) and no deuterium had been incorporated into the methyl groups.

EXAMPLE 21

The preceeding perdeuterated o-xylene of example 20 (45g, containing 3.50 deuterium atoms) was treated with a fresh batch 140 ml of 4% DCl in D$_2$O in a glass tube for 42 hours at 250° C. Deuterium assay by mass spectometer established that the resultant o-xylene (45g, 100% yield, >95% purity) was composed of 3.7% d$_5$, 87.3%d$_4$, 4.7%d$_3$ and 3.4%d$_2$ species (total 3.90 atoms of deuterium). Using methanol as an internal standard, n.m.r. area integration established that there were 3.91 deuterium atoms (98% exchange) in the atomatic ring and 0.06 deuterium atoms in the methyl groups.

EXAMPLES 22–24

Table 5 below shows comparable results obtained by application of the process of m-xylene substrate. In a typical example 0.29g of m-xylene and 4 ml of the acid were introduced into a glass tube, and the sample degassed three times by the freeze-pump-thaw method, sealed and heated at 250° for the necessary time. The colourless reaction mixture was diluted with water (4 ml), neutralized with solid solium bicarbonate and extracted with ether (4 × 10ml). The ether extract was dried and concentrated on a rotatory evaporator. Analytical gas/liquid phase chromatography (g.l.p.c.) showed m-xylene as the only product.

TABLE 5

| Ex. | Acid V/V | Temp° C | Time (h) | D/Mol. | D/Posn | % Yield |
| --- | --- | --- | --- | --- | --- | --- |
| 22 | 10% CH$_3$COOD | 250 | 48 | 0.94 | ring | — |
| 23 | 10% CH$_3$COOD+ 1% HCl | 250 | 53 | 3.62 | 3.32 ring 0.30 methyl | — |
| 24 | 4% HCl | 250 | 40 | 3.96 | 3.64 ring 0.32 methyl | >95% |

EXAMPLE 25

0.60g of pyridine and 5ml of 4% V/V conc. HCl in D$_2$O were introduced into a glass tube (10 in × 0.5 in); the sample was degassed three times by the freeze-pump-thaw method, sealed and heated at 250° in the Pressure Reaction Apparatus. After 48 hours the cooled black reaction mixture was basified with solid sodium bicarbonate, extracted with ether (4 × 15 ml), dried and concentrated on a rotatory evaporator. The dark brown extract was transferred quantitatively into a 1 ml volumetric flask and made up to volume. G.l.p.c. analysis established that the extract contained 95% pyridine and 5% of three unidentified products.

Preparative g.l.p.c. (using a liquid air cooled U-tube for collection) established that the isolable yield of pyridine was 0.14g (23%). Mass spectrometric analysis at 15 eV of the pyridine collected by g.l.p.c. established that it was composed of 45.7% d$_5$, 36.4% d$_4$, 14.2% d$_3$, and 3.6% d$_2$ species, a total of 4.25 deuterium atoms per molecule (84% exchange). N.m.r. integral analysis showed that equilibration of the position was complete.

EXAMPLES 26 to 31

Table 6 below shows the results obtained using aniline as the substrate but employing the hydrochloride salt as the starting material without the need for additional acid. It is found that the quantity of acid in the molecule is sufficient under the conditions of the process to effect the necessary exchange when the salt is dissolved in D$_2$O. Under the higher temperatures of the range for the processes of the invention the produce is not deuterated aniline alone, but instead is a mixture of deuterated aniline and phenol.

TABLE 6

| Ex. | Temp.° C | Time (h) | D/mol. | % Exchange in aromatic ring | Position o | Position m | Position p | % Yield |
| --- | --- | --- | --- | --- | --- | --- | --- | --- |
| 26 | 175 | 24 | 2.85 | 57 | 1.90 | 0.0 | 0.95 | 86 |
| 27 | 250 | 12 | 3.60 | 72 | 1.85 | 0.80 | 0.95 | 74 |
| 28 | 250 | 35 | 4.60 | 92 | 1.90 | 1.75 | 0.95 | 72 |
| 29 | 250 | 54 | 4.75 | 95 | 1.90 | 1.90 | 0.95 | 69 |
| 30 | 250 | 48 | 4.15 | 83 | 1.75 | 1.55 | 0.85 | 82 |
| 31 | 250 | 50 | 4.85 | 97 | 1.95 | 1.95 | 0.95 | 72 |

For examples 26 to 29 a solution of the recrystallized substrate in D$_2$O was degassed three times and heated in a sealed tube.

In the procedure used for examples 30 and 31, freshly recrystallized aniline hydrochloride (20.0g) was first stirred with 50 ml of D$_2$O at room temperature for several hours in order to avoid dilution of the deuterium pool by the amino protons. The D$_2$O was then distilled off under vacuum and recovered for use in the first cycle of subsequent exchanges. The amino exchanged aniline hydrochloride was dissolved in 60 ml of fresh deuterium oxide and sealed in a glass tube after being degassed three times. The tube was heated at 250° in a 2-liter pressure apparatus containing H$_2$O to equalize the internal pressure. After 48 hours, the D$_2$O and traces of phenol were distilled off under vacuum to leave 16.4g of a yellowish solid (82%) yield. N.m.r. integral analysis of an aliquot established the following deuterium distribution; 1.75, 1.55 and 0.85 at the ortho-, meta- and para-positions respectively (83% exchange).

The crude aniline hydrochloride (16.4g) for example 30 was used in example 31 by heating at 250° with 60ml of fresh D$_2$O. After 50 hours the D$_2$O was again reclaimed by vacuum distillation to leave a yellowish solid. This solid was dissolved in H$_2$O and then basified with concentrated NaOH and extracted with ether. This ether extract was washed with 10% HCl. The aqueous HCl phase, containing the anilinium sale, was basified with concentrated NaOH and extracted with ether. The ether extract was washed with water and dried. After removal of solvent, vacuum distillation yielded 10.25g aniline-d$_5$, resulting in a 75% overall yield after two cycles. N.m.r. analysis showed that all the aromatic positions had been equilibrated with 97% exchange.

Other amine/acid combinations which exist as stable compounds under normal conditions can of course be used.

EXAMPLE 32

5.0g of diphenylamine was mixed with 3.7 ml conc. DCl in 120 ml D$_2$O (3.1% V/V) and the solution was degassed, sealed in a glass tube and heated as described for previous examples for 48 hours at 250° C. The tube was opened, the yellowish solution transferred to a separator funnel and adjusted to pH 8–10 with solid potassium hydroxide. The solution was extracted with 30°–60° petroleum-ether containing 1% ether (c × 75 ml). The organic layers were washed with dilute aqueous KOH (2 × 50 ml), dried and the solvent evaporated to give 1.3g of a pale yellow solid. N.m.r. integral analysis (using the back exchanged N-H as the standard) showed that the aromatic positions were 96–97% deuterated, corresponding to complete equilibration with the deuterium pool. The $D_2O$ layer was acidified with conc. HCl and extracted with ether (1 × 100, 2 × 50 ml). The ether layers were dried and the solvent was evaporated to give deuterated phenol (2.0g). In order to minimize the conversion of the amine to phenol a shorter reaction time of approximately 30–35 h would be required.

EXAMPLE 33

0.98g of 2,6-dimethylaniline was mixed with 0.5ml conc. DCl 9.5 ml $D_2O$ (5.3% V/V), the solution was degassed via two freeze-pump-thaw cycles and sealed under vacuum. The solution was heated for 22 hours at 250° C, the tube was opened and solution was basified with two pellets of solid NaOH and extracted with ether (1 × 20 ml). The ether layer was washed with water (2 × 10 ml) and dried. Evaporation of the solvent gave 0.7g of viscous oil consisting of 2,6-Dimethyl-3,4,5-trideuteroaniline. N.m.r. integral analysis, using the methyl group resonances as the standard since the methyl groups do not exchange, established that the material was 97% exchanged at the aromatic positions. This corresponds to complete equilibration of the hydrogens on the aromatic system with the deuterium pool. The $D_2O$ layer was acidified with conc. HCl and extracted with ether (2 × 10ml). The ether layers were dried and evaporated to give a trace (< 0.005g) of a white solid.

The 2,6-dialkylated anilines constitute the aromatic portion of commonly used local anaesthetics of the xylocaine type, and tagging of this type in the nucleus permits effective study of their biochemistry within the body.

EXAMPLE 34

2.0g of chlorobenzene was mixed with 0.8 ml conc. DCl in 20 ml $D_2O$ (4% V/V), the solution was degassed twice and sealed in a thick-walled glass tube under vacuum and heated for 44 hours at 250° C in the pressure apparatus. The tube was opened and the clear colourless 3,4,5-trideuterochlorobenzene (1.9g) was withdrawn with a pipette. Proton n.m.r. integral analysis, as described previously, showed that exchange was 60% complete. $^{13}C$ n.m.r. analysis showed that the exchange had occurred selectively at the ortho and para positions only.

EXAMPLE 35

0.5g of chlorobenzene was mixed with 0.4ml of conc. DCl and 9.6 ml $D_2O$ and the solution was degassed twice, sealed under vacuum in a glass tube and heated for 23 hours at 275° C. The tube was opened and the clear colourless liquid (0.48g) perdeuterated chlorobenzene was removed with a pipette and analyzed for deuterium incorporation by n.m.r. integral analysis using acetone (weighed with a known amount of chlorobenzene) as the standard. The analysis showed the exchange was 85% complete. Only a longer reaction time would be required to accomplish complete exchange.

We claim:
1. A process for the deuteration or tritiation of organic substrates containing at least one unsaturated aromatic ring selected from benzene rings and pyridine rings by hydrogen substitution and being capable of carbonium ion formation, wherein the substrate is subjected to the effects of a 0.10 to 10% v/v dilute solution of a strong acid in deuterium or tritium oxide respectively at a temperature between 200° and 400° C.
2. A process as claimed in claim 1 wherein the substrate is subjected to the effect of a 0.10 to 4% V/V solution of the acid in the deuterium or tritium oxide respectively.
3. A process as claimed in claim 1 wherein the substrate is subjected to the effect of a 0.25 to 4% V/V solution of the acid in the deuterium or tritium oxide respectively.
4. A process as claimed in claim 1, wherein the process is carried out at a temperature between 200° and 350° C.
5. A process as claimed in claim 1, wherein the acid is a deuterated acid.
6. A process as claimed in claim 1, wherein the acid is any one of ACl; ABr; $A_2SO_4$; $A_3PO_4$; $CF_3COOA$ and $CH_3COOA$, where A is any one of hydrogen, deuterium or tritium.
7. A process as claimed in claim 1, wherein the substrate is subjected during the process to a pressure of about from 100 to 3,000 p.s.i.
8. A process as claimed in claim 1, wherein the substrate is a composition comprising a linked amine and acid, and the acid is freed by decomposition of the substrate under the conditions of operation of the process to enter the said dilute solution.
9. A process for the deuteration or tritiation of a cyclic organic substrate by hydrogen substitution, the substrate containing unsaturation and being capable of carbonium ion formation at the site of the double bond, the said substrate having a benzene nucleus, and wherein the substrate is subjected to the effects of a 0.10 to 10% V/V dilute solution of a strong acid in deuterium or tritium oxide respectively at a temperature between about 200° and 400° C.
10. A process as claimed in claim 1 wherein the substrate is selected from benzene, aniline, phenol, benzoic acid, toluene, xylene, chlorobenzene, biphenyl, diphenylamine, dimethyl aniline and pyridine.

* * * * *